United States Patent [19]

Alario et al.

[11] Patent Number: 5,789,641
[45] Date of Patent: Aug. 4, 1998

[54] PROCESS FOR DISMUTATION AND/OR TRANSALKYLATION OF ALYKLAROMATIC HYDROCARBONS IN THE PRESENCE OF TWO ZEOLITIC CATALYSTS

[75] Inventors: Fabio Alario, Neuilly sur Seine; Eric Benazzi, Montesson, both of France

[73] Assignee: Institut Francais du Petrole, France

[21] Appl. No.: 796,118

[22] Filed: Feb. 6, 1997

[30] Foreign Application Priority Data

Feb. 9, 1996 [FR] France ................................ 96 01608

[51] Int. Cl.$^6$ ............................................. C07C 5/22
[52] U.S. Cl. ............................... 585/475; 585/474
[58] Field of Search .................... 585/470, 474, 585/475

[56] References Cited

U.S. PATENT DOCUMENTS

| | | | |
|---|---|---|---|
| 3,506,731 | 4/1970 | Frilette et al. | 260/672 |
| 3,548,020 | 12/1970 | Gutberlet et al. | 585/474 |
| 4,774,377 | 9/1988 | Barger et al. | 585/323 |
| 5,177,280 | 1/1993 | Jurguin et al. | 585/323 |
| 5,198,595 | 3/1993 | Lee et al. | 585/467 |
| 5,210,356 | 5/1993 | Shamshoum et al. | 585/475 |

FOREIGN PATENT DOCUMENTS

| | | |
|---|---|---|
| 2 291 957 | 6/1976 | France . |
| 2 303 782 | 10/1976 | France . |
| 25 58 035 | 6/1977 | Germany . |

OTHER PUBLICATIONS

U.S. application No. 08/796,944, Attorney Docket No. PET 1429, Use of Composite Catalyst for the Dismutation and/or Transalkylation of Alkylaromatic Hydrocarbons, Alario et al.

U.S. application No. 08/797,286, Attorney Docket No. PET 1428, A Catalyst Comprising a Zeolite of Structure Type Mazzite and Its Use for the Dismutation and/or Transalkylation of Alkylaromatic Hydrocarbons, Benazzi et al.

U.S. application No. 08/797,786, Attorney Docket No. PET 1426, Zeolite Based Catalyst of Modified Mazzite Structure Type and Its Use for the Dismutation and/or Transalkylation of Alkylaromatic Hydrocarbons, Benazzi et al.

U.S. application No. 08/796,188, Attorney Docket No. PET 1427, Use of an Omega Zeolite Based Catalysts Comprising One Metal from Groups IIA, IVB, IIB, or IVA for the Dismutation and/or Transalkylation of Alkylaromatic Hydrocarbons, Benazzi et al.

Primary Examiner—Glenn Caldarola
Assistant Examiner—Thuan D. Dang
Attorney, Agent, or Firm—Millen, White, Zelano & Branigan, P.C.

[57] ABSTRACT

The invention concerns the dismutation of alkylaromatic hydrocarbons, preferably the dismutation of toluene to produce benzene and xylenes, and/or the transalkylation of alkylaromatic hydrocarbons, preferably the transalkylation of toluene and trimethylbenzenes to produce xylenes, in a reaction zone comprising at least two catalytic beds each comprising a different catalyst, one of the catalysts containing at least one zeolite with mordenite type structure, at least partially in its acid form, and the other catalyst containing at least one zeolite with mazzite type structure, at least partially in its acid form, each catalyst containing at least one matrix and, optionally, at least one element selected from the group formed by groups IB and VIII of the periodic classification of the elements.

17 Claims, No Drawings

PROCESS FOR DISMUTATION AND/OR TRANSALKYLATION OF ALYKLAROMATIC HYDROCARBONS IN THE PRESENCE OF TWO ZEOLITIC CATALYSTS

BACKGROUND OF THE INVENTION

The invention concerns the dismutation of alkylaromatic hydrocarbons, preferably the dismutation of toluene to produce benzene and xylenes, and/or the transalkylation of alkylaromatic hydrocarbons, preferably the transalkylation of toluene and trimethylbenzenes to produce xylenes, in a reaction zone comprising at least two catalytic beds each comprising a different catalyst, one of the catalysts containing at least one zeolite with mordenite type structure, at least partially in its acid form, and the other catalyst containing at least one zeolite with mazzite type structure, at least partially in its acid form, each catalyst containing at least one matrix and, optionally, at least one element selected from the group formed by groups IB and VIII of the periodic classification of the elements.

Numerous dismutation and transalkylation catalysts based on mordenite have been described in the prior art. This is the case in U.S. Pat. No. 3,506,731 where a mordenite in its hydrogen form is used, also in French patent application FR-A-2 367 533. This is also the case in U.S. Pat. No. 3,281,483 which mentions mordenites which are exchanged essentially with silver or nickel ions, or in U.S. Pat. No. 3,780,121 which describes a mordenite exchanged with metals from group IB of the periodic classification of the elements and which is characterized by a Si/Al atomic ratio which is in the range 6 to 40; U.S. Pat. No. 3,629,351 also concerns a mordenite containing ions of metals from groups IB, VA, VIA, IIA and VIII of the periodic classification of the elements.

More recently, U.S. Pat. No. 5,210,356 has claimed the use of a toluene dismutation catalyst which comprises an omega zeolite which has been modified by dealuminization and charged with nickel.

U.S. Pat. No. 5,371,311 teaches that a catalyst comprising an omega zeolite synthesised using alkaline cations and an organic agent as an organic structuring agent, then modified by calcining in air, ion exchanges, calcining in the presence of steam and finally by treatment with an aqueous solution of ammonium ions at low pH, results in superior physico-chemical properties and improved catalytic performances in hydrocarbon conversion reactions, in particular dismutation and/or transalkylation of alkylaromatics.

SUMMARY OF THE INVENTION

Surprisingly, the association in one reaction zone of at least two catalytic beds each comprising a different catalyst, one of the catalysts containing at least one zeolite with mordenite type structure, at least partially in its acid form, and the other catalyst containing at least one zeolite with mazzite type structure, at least partially in its acid form, each catalyst containing at least one matrix and, optionally, at least one element selected from the group formed by groups IB and VIII of the periodic classification of the elements, results in improved catalytic performances over prior art catalysts for the dismutation of alkylaromatic hydrocarbons such as toluene, and/or for the transalkylation of alkylaromatic hydrocarbons such as toluene and trimethylbenzenes.

The invention thus concerns a process for the dismutation and/or transalkylation of hydrocarbons in a reaction zone comprising at least two catalytic beds, each comprising a different catalyst, one of the catalysts containing at least one zeolite with mordenite type structure, preferably a mordenite, at least partially and preferably practically completely in its acid form, and the other catalyst containing at least one zeolite with mazzite type structure, preferably omega zeolite, at least partially and preferably practically completely in its acid form, each catalyst containing at least one matrix and, optionally at least one element selected from the group formed by groups IB and VIII of the periodic classification of the elements.

The operating conditions are generally as follows: a temperature which is in the range 250° C. to 600° C., preferably in the range 330° C. to 500° C.; a pressure which is in the range 10 to 60 bar, preferably in the range 20 to 45 bar; a supply space velocity, expressed in kilograms of feed introduced per kilogram of catalyst per hour, in the range 0.1 to 10, preferably in the range 0.5 to 4; and a hydrogen to hydrocarbons molar ratio which is in the range 2 to 20, preferably in the range 3 to 12.

The invention thus concerns a process for the dismutation and/or transalkylation of hydrocarbons in a reaction zone comprising at least two catalytic beds each comprising a different catalyst, one of the catalysts generally comprising between 5 to 95%, preferably between 15% to 90% and more preferably between 25% to 85%, of a zeolite with mordenite type structure and, optionally between 0.01% and 10%, preferably between 0.05% and 7%, and more preferably between 0.10% and 5%, of at least one element selected from the group formed by groups IB and VIII of the periodic classification of the elements, the complement to 100% by weight generally consisting of the matrix of said catalyst, and the other catalyst generally comprising between 5 to 95%, preferably between 15% to 90% and more preferably between 25% to 85%, of a zeolite with mazzite type structure and, optionally between 0.01% and 10%, preferably between 0.05% and 7%, and more preferably between 0.10% and 5%, of at least one element selected from the group formed by groups IB and VIII of the periodic classification of the elements, the complement to 100% by weight generally consisting of the matrix of said catalyst.

For each catalyst, the matrix is generally selected from members of the group formed by clays (for example from natural clays such as kaolin or bentonite), magnesia, aluminas, silicas, titanium oxide, boron oxide, zirconia, aluminium phosphates, titanium phosphates, zirconium phosphates and silica-aluminas, preferably from members of the group formed by aluminas and clays.

The zeolite with mazzite type structure is generally selected from the group formed by omega zeolite, mazzite, LZ-202 zeolite, gallosilicate mazzite zeolite or ZSM-4 zeolite, preferably omega zeolite, with a principal pore diameter of about 7.4 Å and with a monodimensional microporous network ("Atlas of Zeolite Structure Types", W. M. Meier and D. H. Olson, $3^{rd}$ edition, 1992). The zeolite with mazzite type structure is at least partially and preferably practically completely in its acid form, i.e., in its hydrogen form ($H^+$).

The zeolite with mazzite type structure generally has a sodium content of less than 0.6%, preferably less than 0.1% by weight (with respect to the zeolite), comprises silicon and at least one element T selected from the group formed by gallium and aluminium, preferably aluminium, and has an Si/T molar ratio which is in the range 5 to 100, preferably in the range 7 to 80.

The zeolite with mordenite type structure is generally selected from the group formed by mordenite and LZ-211 zeolite, preferably mordenite, and has a principal pore diameter of about 7×6.5 Å and a mono-dimensional microporous network ("Atlas of Zeolite Structure Types", W. M. Meier and D. H. Olson, 3$^{rd}$ edition, 1992).

The zeolite with mordenite type structure is at least partially and preferably practically completely in its acid form, i.e., in its hydrogen form (H$^+$).

The zeolite with mordenite type structure generally has a sodium content of less than 0.2%, preferably less then 0.1% by weight (with respect to the zeolite), comprises silicon and aluminium, and has an Si/Al molar ratio which is in the range 5 to 100, preferably in the range 7 to 80.

The zeolite with mordenite type structure has either small pores or large pores, and can be synthesised both in a hydroxide medium and in a fluoride medium.

The zeolite with mordenite type structure with small pores has a sodium content, with respect to the weight of dry mordenite, which is generally in the range 4% to 6.5%, a global Si/Al atomic ratio which is generally in the range 4 to 7, an elementary cell volume which is generally in the range 2.76 to 2.80 nm$^3$ (1 nm=$10^{-9}$ m) and normally only adsorbs molecules with a kinetic diameter of less than about $4.4 \times 10^{-10}$ m.

The zeolite with mordenite type structure with large pores, synthesised in an OH$^{31}$ or F$^-$ medium, for example as described in EP-A-0 427 579, is distinguished from the small pore type in that it can adsorb molecules with a kinetic diameter of more than about $6.6 \times 10^{-10}$ m, (thus it can adsorb benzene molecules), and its global Si/Al atomic ratio is generally in the range 4.5 to 20.

It may be necessary to bring the global Si/Al ratio of the zeolite with mordenite type structure to values which are higher than those obtained during synthesis and mentioned above. In order to obtain dealuminized zeolites with mordenite type structure with a wide range of Si/Al ratios, any method which is known to the skilled person can be used, such as direct acid attack or at least one dealuminization cycle comprising at least one calcining step, which may or may not be in the presence of steam, of the NH$_4^+$ form of the zeolite, followed by at least one acid attack step. In the specific case of the zeolite with mordenite type structure with small pores, it should be ensured that the treatments used lead to channel opening.

The zeolite with mordenite type structure is generally prepared by putting it into its ammonium (NH$_4^+$) form either using an unrefined synthesised zeolite with structure type mordenite in its sodium form, by carrying out a plurality of ion exchange steps using concentrated (10N) ammonium nitrate solutions to obtain a sodium content which is generally less than 2000 ppm by weight, preferably 1000 ppm by weight, more preferably less than 500 ppm by weight, with respect to the dry zeolite with structure type mordenite, or using a dealuminized zeolite with structure type mordenite, by carrying out a plurality of successive ion exchange steps using ammonium nitrate to obtain the NH$_4^+$ form of the zeolite.

After this treatment, the modified zeolite with mordenite type structure generally undergoes heat treatment to decompose the ammonium cations present in the network at least partially and preferably practically completely, and thus obtain the acid form (H-M) of the zeolite with structure type mordenite, at least partially and preferably practically completely.

The zeolite with mordenite type structure can optionally be modified after synthesis, for example by dealuminization by means of at least one treatment with at least one solution comprising at least one fluorosilicate salt such as ammonium hexafluorosilicate, as described in European patent application EP-A-0 573 347 or U.S. Pat. No. 4,503,023, or using at least one compound of elements selected from the group formed by groups IIA, IIB or IVA of the periodic classification of the elements, as described in European patent application EP-A-0 569 268 or U.S. Pat. No. 5,391,528.

Whether it is in its sodium, ammonium or hydrogen form, the zeolite with mordenite type structure can optionally have deposited on it at least one element selected from the group formed by groups IB and VIII of the periodic classification of the elements, preferably selected from the group formed by silver, nickel and platinum, more preferably nickel, and can be formed using any technique which is known to the skilled person.

The zeolite with mazzite type structure is produced using any method which is known to the skilled person, from an unrefined synthesised zeolite with mazzite type structure in which the Si/T ratio is generally in the range 3 to 5.

It is generally necessary to bring the Si/T ratio of the zeolite with mazzite type structure to a value which is higher than that of the unrefined synthesised zeolite with mazzite type structure mentioned above. Any method which is known to the skilled person can be used to obtain zeolites with mazzite type structure with a wide range of Si/T ratios, in particular dealuminization using the method described in U.S. Pat. No. 4,780,436 in the preferred case when T is, i.e., a calcining step is carried out in a stream of dry air, to eliminate the organic structuring agent occluded in the microporosity of the zeolite, followed by at least one ion exchange step using at least one NH$_4$NO$_3$ solution, to eliminate practically all alkaline cations, in particular sodium, present in the cationic position in the zeolite, then at least one framework dealuminization cycle comprising at least one calcining step in the presence of steam at a temperature which is generally in the range 550° C. to 850° C., followed by at least one acid attack step.

In the preferred case when T is aluminium, framework dealuminization, comprising at least one calcining step carried out in steam and at least one attack step in an acid medium for the zeolite with mazzite type structure, can be repeated as many times as is necessary to obtain the dealuminized zeolite with structure type mazzite with the desired characteristics. Similarly, following calcining in steam, a number of successive acid attack steps using different concentrations of acid solutions can be carried out.

Each of the catalysts can be prepared using any method which is known to the skilled person. The description given below can be applied to each of the catalysts.

In general, each catalyst is obtained by mixing the matrix and the zeolite then forming. The optional element from the group formed by groups IB and VIII of the periodic classification of the elements can be introduced either before forming, or during mixing, or to the zeolite itself before mixing, or, as is preferable, after forming. Forming is generally followed by calcining, generally at a temperature which is in the range 250° C. to 600° C. The optional element from the group formed by groups IB and VIII of the periodic classification of the elements can be introduced after said calcining step. In all cases, the element is generally chosen to be deposited either, as is preferable, practically completely on the zeolite, or practically completely on the matrix, or partially on the zeolite and partially on the matrix, the choice being effected, in a manner which is known to the skilled person, by means of the parameters used during said deposition, such as the nature of the precursor selected to effect said deposition.

The element from groups IB or VIII, preferably selected from the group formed by Ag, Ni and Pt, and more preferably Ni, can also be deposited on the zeolite-matrix mixture which has been pre-formed using any procedure which is known to the skilled person. Such deposition is generally carried out by the techniques of dry impregnation, ion exchange(s) or co-precipitation. When ion exchange is carried out using precursors based on silver, nickel or platinum, the salts which are generally used are silver salts such as chlorides or nitrates, a tetramine complex of platinum, or nickel salts such as chlorides, nitrates, acetates or formates. The ion exchange technique can also be used to deposit the metal directly on the zeolite powder before optional mixing with a matrix.

When the catalyst contains a plurality of metals, these latter can be introduced either in the same way or using different techniques, before or after forming and in any order. When the technique used is ion exchange, a plurality of successive exchanges may be necessary to introduce the required quantities of metals.

As an example, one preferred method for preparing the catalyst of the invention consists of mixing the zeolite in a wet matrix gel (generally obtained by mixing at least one acid and a matrix powder), for example alumina, for the time required to obtain good homogeneity of the paste thus produced, i.e., for about ten minutes, for example, then passing the paste through a die to form extrudates with a diameter which is, for example, in the range 0.4 to 4 mm. After oven drying for several minutes at 100° C. and after calcining, for example for 2 hours at 400° C., the optional element, for example nickel, can be deposited, for example by ion exchange, said deposit being followed by final calcining, for example for 2 hours at 400° C.

The catalyst of the invention is generally formed so that the catalyst is preferably in the form of pellets, aggregates, extrudates or spherules, depending on its use.

Catalyst preparation is generally finished by calcining, termed final calcining, normally at a temperature which is in the range 250° C. to 600° C., preferably preceded by drying, for example oven drying, at a temperature which is generally in the range from ambient temperature to 250° C., preferably in the range 40° C. to 200° C. The drying step is preferably carried out during the period of temperature rise required to carry out the calcining step.

The invention concerns the use of the catalyst for the dismutation of alkylaromatic hydrocarbons, preferably for the dismutation of toluene to produce benzene and xylenes, and/or for the transalkylation of alkylaromatic hydrocarbons, preferably for the transalkylation of generally $C_9^+$alkylaromatic hydrocarbons (i.e., containing at least 9 carbon atoms per molecule), such as the transalkylation and/or dismutation of toluene and/or $C_9^+$alkylaromatics to produce xylenes. The feed for such a process can comprise 0 to 100% of $C_9^+$alkylaromatics and 0 to 100% of toluene.

The operating conditions are generally as follows: a temperature which is in the range 250° C. to 600° C., preferably in the range 330° C. to 500° C.; a pressure which is in the range 10 to 60 bar, preferably in the range 20 to 45 bar; a supply space velocity, expressed in kilograms of feed introduced per kilogram of catalyst per hour, in the range 0.1 to 10, preferably in the range 0.5 to 4; and a hydrogen to hydrocarbons molar ratio which is in the range 2 to 20, preferably in the range 3 to 12.

The following examples illustrate the invention without in any way limiting its scope.

EXAMPLE 1

Preparation of Catalyst M1

The starting material used was a mordenite with a global Si/Al atomic ratio of 7.6, a sodium content of about 3.8% with respect to the weight of dry mordenite, an elementary cell volume of 2.759 nm$^3$ and a pore volume in nitrogen of 0.192 cm$^3$ liquid per gram, measured at −196° C. and at $P/P_0$=0.19.

This mordenite underwent acid attack with 5N nitric acid at about 100° C. for 4 hours, to partially extract the aluminium atoms present in the zeolitic framework of the mordenite. The volume V of the nitric acid used (in ml) was 10 times the weight W of the dry omega zeolite (V/W=10). The dealuminized mordenite zeolite then underwent ion exchange in a 10N $NH_4NO_3$ solution at about 100° C. for 4 hours to extract the residual sodium.

At the end of these treatments, the mordenite in its H form had a global Si/Al atomic ratio of 26.3, a sodium content of 72 ppm by weight with respect to the weight of dry mordenite, an elementary cell volume of 2.722 nm$^3$ and a nitrogen adsorption capacity of 0.204 cm$^3$ of liquid/g, measured at −196° C. and at $P/P_0$=0.19.

This mordenite was then formed by extrusion with an alumina gel to obtain catalyst M1 which contained 80.2% of mordenite in its hydrogen form and 19.8% of alumina, after drying and calcining in dry air.

EXAMPLE 2

Preparation of Catalyst Ω1

The starting material used was an omega zeolite with a global Si/Al atomic ratio of 3.2, a sodium content of about 5.3% with respect to the weight of dry omega zeolite, an elementary cell volume of 2.196 nm$^3$ and a pore volume in nitrogen of 0.125 cm$^3$ liquid per gram, measured at −196° C. and at $P/P_0$=0.19.

This omega zeolite was initially "dry" calcined at 550° C. in a stream of air and nitrogen for 6 hours. The solid obtained was then subjected to three ion exchange steps in a 10N $NH_4NO_3$ solution at about 100° C. for 4 hours for each exchange step. The omega zeolite then underwent hydrothermal treatment in the presence of 50% of steam at 600° C. for 4 hours. The zeolite underwent acid attack with 1N nitric acid at about 100° C. for 2 hours, to extract the extra-network aluminium species formed during hydrothermal treatment. The volume V of the nitric acid used (in ml) was 10 times the weight W of the dry omega zeolite (V/W=10). The treated omega zeolite then again underwent hydrothermal treatment in the presence of 50% steam, this time at 700° C. for 4 hours, then acid attack with a 1.5N nitric acid solution at about 100° C. for 4 hours to extract the extra-network aluminium species formed during hydrothermal treatment. The volume V of the nitric acid used (in ml) was 10 times the weight W of the dry omega zeolite (V/W=10).

At the end of these treatments, the omega zeolite in its H form had a global Si/Al atomic ratio of about 25, a sodium content of 90 ppm by weight with respect to the weight of dry omega zeolite, an elementary cell volume of 2.115 nm$^3$ and a nitrogen adsorption capacity of 0.206 cm$^3$ of liquid $N_2$/g, measured at −196° C. and at $P/P_0$=0.19.

This omega zeolite was then formed by extrusion with an alumina gel to obtain catalyst Ω1 which contained 80.2% of omega zeolite in its hydrogen form and 19.8% of alumina, after drying and calcining in dry air.

EXAMPLE 3

Preparation of Catalyst M2

Catalyst M1 obtained from Example 1 underwent three ion exchange steps with a nickel acetate solution to introduce 1.0% by weight of nickel into the catalyst.

To this end, catalyst M1 was brought into contact with a 0.5M solution of $Ni(CH_3CO_2)_2$ at ambient temperature and with stirring. The solid was separated from the impregnating solution and washed with abundant quantities of deionised water between each exchange. The concentration of the impregnating solution was re-adjusted to a concentration of 0.5 moles per litre for each exchange step.

The wet solid was dried at 120° C. for 12 hours and calcined in a stream of dry air at 500° C. for 1 hour. Catalyst M2 obtained contained 79.3% of mordenite in its hydrogen form, 19.6% of alumina and 1.1% of nickel.

EXAMPLE 4

Preparation of Catalyst Ω2

Catalyst Ω1 obtained from Example 2 underwent three ion exchange steps with a nickel acetate solution to introduce 1.0% by weight of nickel into the catalyst.

The operating conditions for the ion exchange steps, washing, drying and calcining were identical to those described in Example 3.

Catalyst Ω2 obtained contained 79.5% by weight of omega zeolite, 19.6% by weight of alumina and 0.9% by weight of nickel.

The following table summarises the compositions of catalysts M1 from Example 1, Ω1 from Example 2, M2 from Example 3, and Ω2 from Example 4:

| Catalysts | Mordenite zeolite (wt %) | Omega zeolite (wt %) | Nickel (wt %) | Alumina (wt %) |
|---|---|---|---|---|
| M1 | 80.2 | 0.0 | 0.0 | 19.8 |
| Ω1 | 0.0 | 80.2 | 0.0 | 19.8 |
| M2 | 79.3 | 0.0 | 1.1 | 19.6 |
| Ω2 | 0.0 | 79.5 | 0.9 | 19.6 |

EXAMPLE 5

Evaluation of Catalyst Performances

The catalysts were used in a fixed bed reactor under pressure, into which the feed, constituted by pure toluene, was introduced.

The table below compares the yields of (benzene+ethylbenzene+xylenes) obtained using two beds of a catalyst comprising one bed of catalyst M1 (respectively M2) and one bed of catalyst Ω1 (respectively Ω2), in accordance with the invention, and one bed of catalyst M1 (respectively M2) and one bed of catalyst Ω1 (respectively Ω2), not in accordance with the invention:

| Catalysts | M1 (not invention) | Ω1 (not invention) | M1 + Ω1 bed1 bed2 (invention) | M2 (not invention) | Ω2 (not invention) | M2 + Ω2 bed1 bed2 (invention |
|---|---|---|---|---|---|---|
| Reaction temperature (°C.) | 450 | 450 | 450 | 430 | 430 | 430 |
| Total reaction pressure (bar) | 30 | 30 | 30 | 40 | 40 | 40 |
| Yields, % by weight (benzene + ethylbenzene + xylenes) | 43.4 | 38.9 | 43.6 | 42.2 | 36.9 | 42.5 |

Thus the process of the invention results in superior (benzene+ethylbenzene+xylenes) yields.

We claim:

1. A process for the dismutation and/or transalkylation of alkylaromatic hydrocarbons in a reaction zone comprising at least two catalytic beds each comprising a different catalyst, one of the catalysts containing at least one mordenite zeolite at least partially in its acid form, and the other catalyst containing at least one mazzite zeolite at least partially in its acid form, each catalyst containing at least one matrix and, optionally, at least one element selected from the group formed by groups IB and VIII of the periodic classification of the elements.

2. A process according to claim 1, carried out in a reaction zone comprising at least two catalytic beds each containing a different catalyst, one of the catalysts generally comprising between 5% and 95% of a mordenite zeolite and, optionally between 0.01% and 10% of at least one element selected from the group formed by groups IB and VIII of the periodic classification of the elements, and remainder to 100% consisting essentially of the matrix in said catalyst, and the other catalyst generally comprising between 5% and 95% of a mazzite zeolite and, optionally between 0.01% and 10% of at least one element selected from the group formed by groups IB and VIII of the periodic classification of the elements, and remainder to 100% consisting essentially of the matrix in said catalyst.

3. A process according to claim 1 in which, for each catalyst, the matrix is selected from the group formed by clays, magnesia, aluminas, silicas, titanium oxide, boron oxide, zirconia, aluminium phosphates, titanium phosphates, zirconium phosphates and silica-aluminas.

4. A process according to claim 1 in which, for each catalyst, said element is selected from the group formed by Ag, Pt and Ni.

5. A process according to claim 1, in which the mazzite zeolite is selected from the group formed by gallosilicate mazzite zeolite, mazzite, LZ-202 zeolite, omega zeolite, and ZSM-4 zeolite.

6. A process according to claim 1, in which the mazzite zeolite is omega zeolite.

7. A process according to claim 1, in which the mazzite zeolite is practically completely in its acid form.

8. A process according to claim 1, in which the mazzite zeolite has a sodium content of less than 0.6% by weight (with respect to said zeolite), contains silicon and aluminium, and has an Si/Al molar ratio which is in the range 5 to 100.

9. A process according to claim 1, in which the mordenite zeolite is selected from the group formed by mordenite, and LZ-211 zeolite.

10. A process according to claim 1, in which said mordenite zeolite is mordenite.

11. A process according to claim 1, in which the mordenite zeolite is practically completely in its acid form.

12. A process according to claim 1, in which the mordenite zeolite has a sodium content of less than 1% by weight (with respect to said zeolite), contains silicon and aluminium, and has an Si/Al molar ratio which is in the range 5 to 100.

13. A process according to claim 1, in which the catalyst is in the form of pellets, aggregates, extrudates or spherules.

14. A process according to claim 1, in which the operating conditions are as follows: a temperature which is in the range 250° C. to 600° C.; a pressure which is in the range 10 to 60 bar; a space velocity, expressed in kilograms of feed introduced per kilogram of catalyst per hour, which is in the range 0.1 to 10, and a hydrogen to hydrocarbons molar ratio which is in the range 2 to 20.

15. A process according to claim 1, for the dismutation and/or transalkylation of toluene and/or alkylaromatics containing at least 9 carbon atoms per molecule.

16. A process according to claim 1, for the dismutation and/or translakylation of toluene.

17. A process according to claim 16, wherein the at least one mordenite catalyst comprises mordenite in its hydrogen form and alumina; and the at least one suggests catalyst comprises omega zeolite and alumina.

* * * * *